United States Patent [19]

Tributsch et al.

[11] Patent Number: 4,704,576
[45] Date of Patent: Nov. 3, 1987

[54] MICROWAVE MEASURING AND APPARATUS FOR CONTACTLESS NON-DESTRUCTIVE TESTING OF PHOTOSENSITIVE MATERIALS

[75] Inventors: Helmut Tributsch; Gerhard Beck; Marinus Kunst, all of Berlin, Fed. Rep. of Germany

[73] Assignee: Hahn-Meitner-Institut für Kernforschung Berlin GmbH, Berlin, Fed. Rep. of Germany

[21] Appl. No.: 706,712

[22] Filed: Feb. 28, 1985

[30] Foreign Application Priority Data

Feb. 29, 1984 [DE] Fed. Rep. of Germany ....... 3407850

[51] Int. Cl.⁴ ..................... G01R 31/26; G01R 27/06
[52] U.S. Cl. .............................. 324/158 R; 324/58 B; 324/158 D
[58] Field of Search ........... 324/158 R, 158 D, 158 T, 324/58 B, 95

[56] References Cited

U.S. PATENT DOCUMENTS 3,939,415  2/1976  Terasawa .................... 324/158 R Primary Examiner—Ernest F. Karlsen
Attorney, Agent, or Firm—McGlew and Tuttle

[57] ABSTRACT

Variations in parameters of a waveguide system caused by an excitation of charge carriers of a specimen to be measured and positioned in a microwave field, give definite information on the material properties of the specimen without having to destroy, or even contact the specimen. Irradiation with a sharply focused photon or electron beam of a surface spot having a diameter of about 0.1 to 10.0 micrometers, and displacing of this light spot across the surface of the specimen, with the displacement increments of the specimen within the cross sectional area of a waveguide being of the order of magnitude of micrometers, surface structures such as ground boundaries, steps in stratified-lattice crystals, formation defects, destroyed surface areas, etc., can be detected in photosensitive semiconductor layers with a high resolution.

21 Claims, 9 Drawing Figures

MICROWAVE MEASURING AND APPARATUS FOR CONTACTLESS NON-DESTRUCTIVE TESTING OF PHOTOSENSITIVE MATERIALS

FIELD AND BACKGROUND OF THE INVENTION

The present invention relates in general to a microwave measuring method and apparatus, and in particular to a new and useful contactless and non-destructive testing of photosensitive materials and semiconductor layers, or components or circuits using such layers.

The present invention starts from the prior art such as disclosed for example, in the "Journal of Applied Physics", vol. 30, No. 7, July 1959, page 1054 ff (particularly pages 1057 to 1058). The starting point is that in a semiconductor material, an excess carrier density can be created by irradiation, and that the variations of the microwave field caused by the induced conductivity in this material which is placed in the field, can readily be measured. Consequently, an apparatus for this purpose comprise a waveguide system, a radiation source for creating the charge carrier excess in the photsensitive material, and more or less conventional measuring devices.

U.S. patent application Ser. No. 694,932 filed Jan. 25, 1985, assigned to the owner of the present application is incorporated here by reference and is also based on the possibility of determining the characteristic properties of the material through a nondestructive measuring method interrupting the manufacturing opertions only to an absolutely necessary extent. (At the time of invention, the subject of the present application and Ser. No. 694,932 were co-owned.)

In photoactive and photosensitive materials, the photosensitivity of course is one of the most important properties which can be tested also through a contactless excitation of charge carriers and through their influence on the surrounding microwave field, to infer therefrom the quality of the material.

Any change in the parameters (dielectricity constant, conductivity, etc.) in a waveguide system causes dispersion or absorption, or both, of microwaves. Determination of the parameters of a material from the variations of a microwave field under the influence of this material is known already for a long time (see, for example, "Dielectric Materials and Applications", by A. R. von Hippel, Wiley, N.Y., 1952 or "Measuring of Dielectric Properties of Materials" by A. Rost, Akademie Publishers, Berlin 1978). Already in 1953, these variations in the semiconductor layers had been used for determining the electrical transport properties of these materials (see "Phys. Rev. 89", by T. S. Benedict and W. Shockley, Jan. 16, 1953, p. 1152). The following measuring methods are usual:

(a) Measuring of variations caused by the material, of the proportion of standing waves;
(b) Measuring of the absorption coefficient of the material; or
(c) Measuring of the reflection coefficient of the material (see also "Rev. Sci. Instrum." Vol 44, No. 9, Sept. 1973, p. 1204 ff).

The methods under (b) and (c) permit a well defined evaluation of the parameters only under particular conditions, when the measurement is conducted at a single frequency. In general, the measurements must be numerically evaluated in a certain frequency region.

A measurement of the variations of a microwave field in a wave guide in which photosensitive material is received and exposed to irradiation with electrons or photons (excitation of the electrons beyond the band gap), makes it possible to determine the conductivity in excess produced in the material by the irradiation (see the above mentioned article in "J.Appl.Phys." Vol. 30, No. 7 July 1959). For various reasons, only methods under (b) and (c) are usable in this regard.

With an only slight change in the reflection and absorption coefficients caused by the excess conductivity, it may be shown that the relative variations under irradiation of the reflected and the absorbed microwave power are proportional to this excess conductivity (see "Radiat. Phys. Chem.", Vol. 10, July 1977 pp 353–365, or "Proc. IEEE" 51, 1963 sp. 681 ff). The constant of proportionality is a function of the material properties without irradiation (optical parameters and dimensions) and, in general, is evaluable if measurements can be made over a larger frequency region or with samples of different thickness. However, the evaluation is not needed if only relative variations of the excess conductivity are compared with each other, and the other equilibrium properties (properties without irradiation) of the material do not vary or vary only little. The measured excess conductivity then correlates with the property of the tested material in the photocells.

SUMMARY OF THE INVENTION

The present invention is directed not simply to a general testing of a photosensitive material, components, or the like, but rather the surfaces of layers of such a material are to be tested in a non-destructive and contact-free manner and with a high resolution of microscopic quality.

Accordingly, an object of the present invention is to provide a method for the non-destructive contactless testing of photosensitive materials, semiconductor layers, or components or circuits made up of such layers, wherein a charge carrier excess is created in the photosensitive material by irradiation and the variations in the microwave field produced by the induced conductivity are measured, characterized in that the material placed in the microwave field is irradiated with electrons or protons which are sharply focused onto a discrete area of the material's surface to be tested, and any microstructure or structural defects are determined by varying the irradiation surface area.

A further object of the invention is to provide a microwave measuring apparatus which can be used to practice the inventive method.

The sharply focused radiation produces the effect that charge carriers are produced only in the irradiated part of the material, and the measured excess conductivity is characteristic only of the irradiated portion. Materials with locally varying photoelectric properties then also show locally different microwave absorptions and reflections. If the microwave field outside a waveguide is locally inhomogeneous and excess conductivities at different locations of the material are to be compared with each other, the additional microwave absorption or reflection should, as far as possible, be provided always at the same location of the microwave field, or, instead, a corresponding correction must be introduced.

The following alternatives of putting the inventive method to use, thus testing without destroying or damaging the material, may be considered:

Determining of the surface structure of polycrystalline, photosensitive materials. The excess conductivity is measured with a local resolution and the local variations may show: grain boundaries (smaller or large excess conductivity) steps in the surface (such as in stratified-lattice crystals), chemically inhomogeneous surface structure, structural defects in conductive tracks, etc.

Testing the quality of photocells. Irregularities in the excess conductivity at certain locations of the surface of a photocell may indicate fabrication defects and destruction of the material at these locations.

Testing the quality of microelectronic systems built up of photosensitive semiconductors, plastics, and metals (such as semiconductor chips). A locally resolved sectional excess conductivity pattern of a model product (standard) is compared with a corresponding pattern of the tested product. Defects and descruction areas, and the location thereof, may thus be determined.

This testing may be conducted ex-situ, or also in-situ.

In practice, it is advantageous to provide focusing of the electron and photon beam to a spot having a diameter of about 0.1 to 10 micrometers. Because of the diffusion in the material, the region of induced conductivity becomes larger anyway, so that natural limits are set on the focusing.

Since what is evaluated are relative variations in the microwave field, means must be provided for moving the specimen and the electron or photon beam relative to each other, to make the measurement in the desired local resolution. With in-situ measurements, it is advantageous to fix the specimen in place and move the beam over or across the surface of the material which is placed in the microwave filed. With ex-situ measurements, the material in the microwave field may be moved relative to a stationary beam, so that the irradiated area of the material, even though changing, remains at the same location of the microwave field, i.e. variations in the material at different locations can be determined irrespective of the structure of the microwave field within the waveguide. The movements may also be combined.

The relative movement between the tested material and the beam takes place preferably in steps or increments, in accordance with a predetermined pattern. This makes it possible to obtain a virtually continuous image of the surface structure of the specimen. The steps should be on the order of magnitude of micrometers. A satisfactory resolution can then be obtained. The sharpness of focusing of the electron or photon beam, of course, must be brought in accordance with the dimension of these steps.

In this connection, a particularly advantageous development of the inventive method provides that a photon beam is produced by a cyclically switchable laser. Such a pulsating radiation permits a resolution in time of the measurement, i.e. particularly a partial elimination of irregularities caused by the diffusion of the charge carriers out of the light spot proper into the adjacent material.

A measuring apparatus for carrying out the inventive method, comprises substantially conventional components in a unique combination. This applies to the microwave system proper (waveguide or strip line) as well as to the devices for producing and detecting the microwaves. Further, a suitable radiation source is needed, since the microwave absorption or reflection of irradiated material is to be measured. Specifically, the following sub-assemblies are provided in an apparatus for carrying out the inventive method:

A sample holder for plate-shaped specimens, to position the specimen in the microwave field in a plane forming any desired angle with the direction of propagation of the microwaves;

A sample holder capable of receiving plate-shaped specimens which are to be positioned in a plane which is perpendicular to the direction of propagation of the microwaves, and which cover the waveguide, i.e. extend over the entire cross sectional area thereof; and A beam guiding system for directing the photon or electron beam issuing from a radiation source and sharply focused by means of a focusing device, against a spot on the surface of the plate-shaped speciment within the cross-sectional area of the waveguide.

At the same time, either at least the sample holder must allow a displacement and positioning of the specimen, or at least the beam guiding system must allow a pivoting of the beam, and mutual movements of the specimen and the beam must be made possible.

An inventive measuring apparatus differs from the prior art substantially by making it possible to position a specimen both outside a waveguide, for example at a short distance behind the aperture of a waveguide, behind an antenna, a microwave lens system, etc., and within a waveguide system, and then, for example, in a firmly predetermined orientation, such as perpendicularly to the direction of wave propagation.

For specific applications, a sample holder may be provided with a supporting plate for the specimen, a perforated supporting plate, a plastic supporting plate, a metallic cover plate, and/or perforated cover plate. To produce a pulsating irradiation, a periodically closable shutter may be provided between the source of radiation and the sample holder, or the source may be controlled to produce a cyclic radiation.

Also advantageous is a waveguide elbow, for example, by which the sample holder is supported and which is provided with a radiation window. More particularly, the window may be provided in the outside wall of the elbow, in straight alignment with the center of the area where the sample holder is attached. Such elbows may advantageously be shaped as a 90° knee. If the desired relative movement between the specimen and the beam can be obtained with a movable sample holder alone, thus with the beam fixed, even though at any desired angle of incidence, it is very advantageous to provide an electrically controllable device for displacing the sample holder in two directions of a plane, by micrometer steps. A computer-assisted control for such a displacement device, the source of radiation, and the beam guiding system both create comfortable conditions for the measuring operation and evaluation, and ensure a high, anytime reproducible accuracy.

The invention thus provides a reliable contactless non-destructive method of testing a surface layer of photosensitive or photoactive materials, and an apparatus for practicing the method which is simple in design, rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the following, the operation of a preferred embodiment for and details on the invention, particularly in connection with the measuring apparatus, are explained in more detail with reference to the diagrammatical drawings in which.

DESCRIPTION OF THE PREFERRED EMBODIMENTS

Figure 1:
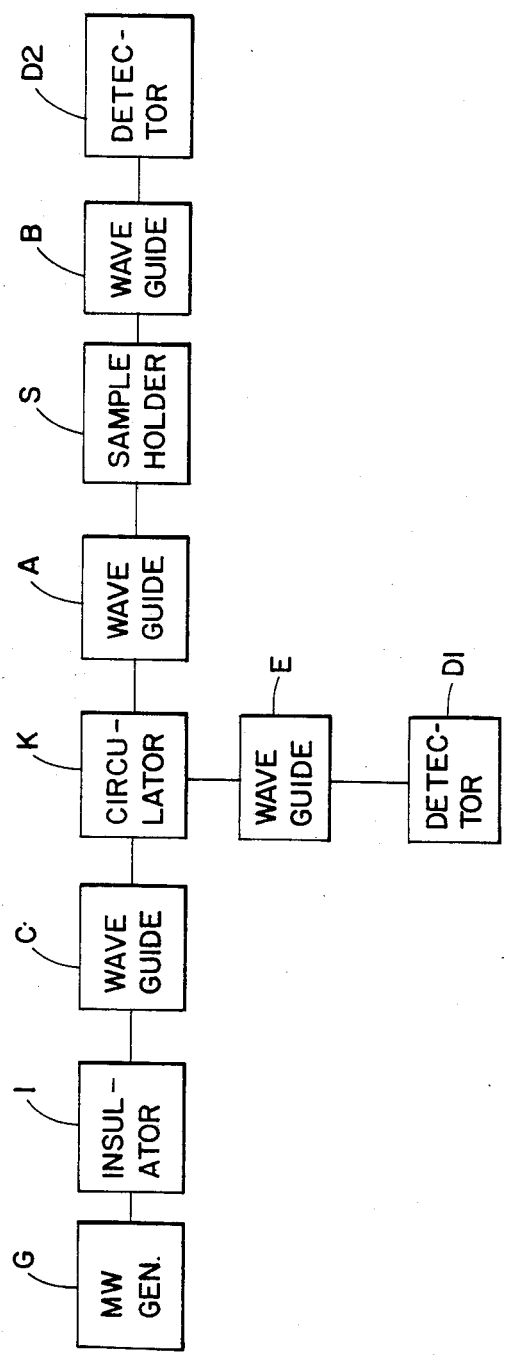
FIG. 1 is a block diagram of the microwave measuring apparatus.

The inventive apparatus makes it possible to detect relative variations of microwave absorptions or reflections of a semi conductor material upon being irradiated with light or electrons. The apparatus substantially comprises three parts:

A waveguide system for producing and detecting the microwaves, which is shown in FIG. 1 as a block diagram and comprises all the components needed under various conditions of application;

A sample holder (particularly shown in FIG. 5); and

Figure 4:
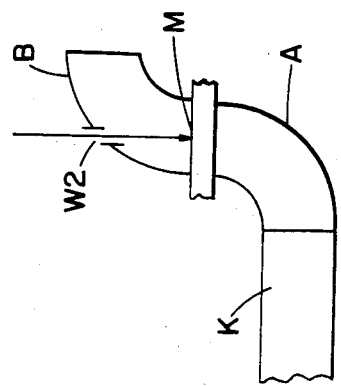
FIGS. 2 to 4, are three side views showing how the beam of radiation may reach the specimen.
Figure 2:
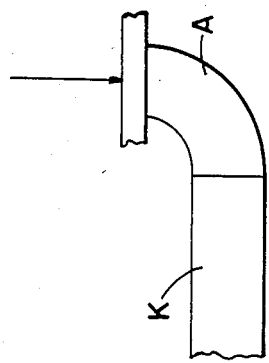
Figure 3:
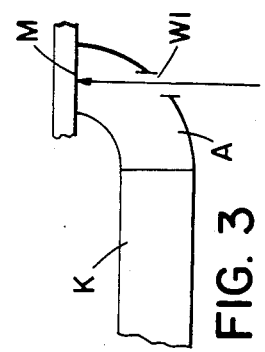

A system of irradiation (particularly shown in FIGS. 2 to 4). The following may be learned from FIG. 1;

The microwaves are produced by a generator G, such as a tunable Gunn diode or a Klystron. They pass through an insulator I, a waveguide C, a circulator or directional coupler K, and another waveguide A, to the sample holder S. The microwaves reflected from the specimen in sample holder S pass back to the circulator (directional coupler K), and the reflected power is transmitted through waveguide E to a detector D1 (semiconductor diode or thermistor) where it is measured. For transmission measurement, still another waveguide B with a detector D2 are provided after sample holder S where the transmitted power is measured. Waveguides B and C are not needed in all instances, and may be omitted.

To induce a conductivity in the material of the sample, the sample is irradiated from one or the other side with light or with electrons. Three variants are shown in FIGS. 2, 3, 4. Variants of FIGS. 2 and 3 are intended for reflection measurements. The samples or specimens always extending over, and even exceeding, the entire cross sectional area of the waveguides, may thus be irradiated from either the side remote from the microwave field, FIG. 2, or from the side facing the field, FIG. 3. In the case of FIG. 2, of course, the waveguide may also extend straight, thus need not be bent as elbow A. In the case of FIG. 3, a radiation window W1 is provided in elbow A through which the beam of radiation passes to the surface of the sample.

If it is intended to irradiate perpendicularly, the window is provided in the outside wall of elbow A in the direction of a normal set up at the center M of the cross sectional area of the waveguide where the sample holder applies thereto.

In the case of FIG. 4, which is intended for transmission measurements, the irradiation may be provided as according to FIG. 3, so that then waveguide B may be straight. The variant of FIG. 4 does not require a bent waveguide A, yet requires a bent waveguide B and a radiation window W2 corresponding to window W1 of elbow A in FIG. 3. The specimen or a sample holder is then fixedly positioned, such as screwed, between waveguides A and B.

Figure 5:
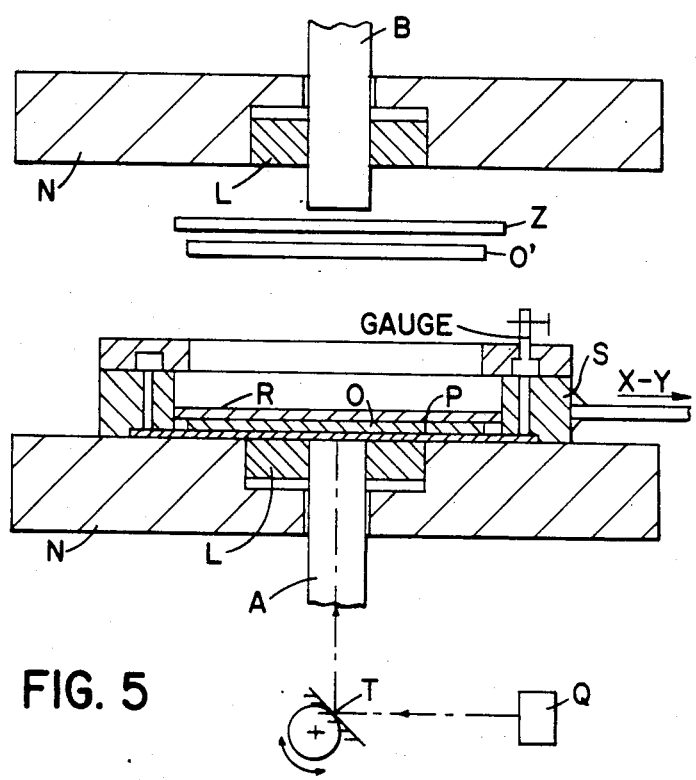
FIG. 5 is a side sectional view of a sample holder with some details shown.

Referring to FIG. 5, showing the sample holder S, it should be noted that the materials whose properties can be measured in this way, generally are substantially two-dimensional plates or layers 0. They are placed across the sectional area of waveguide A and may be pressed into contact therewith. Should the dimension of the specimen be smaller than the area of the aperture, it may be placed on a supporting plate P provided with one or more holes, if necessary, and made of a plastic, for example. To augment the signal, a metallic cover plate R may be provided with one or more holes, which is absolutely necessary if a transmission of microwaves is measured, or if the specimen is irradiated from a metal coated side. A plastic plate, perforated if necessary, may also be provided behind the specimen.

An apparatus for measuring the local variations of the excess conductivity comprises particularly a mechanism with which the sample can be displaced over the cross-sectional area of waveguide A. The end portion of waveguide A where the cross-sectional area is covered by the sample or specimen, for example for reflection measurements, is held in place in a table plane N by means of a body L with which it is displaceable axially.

Sample holder S may be formed by a two-part frame, for example, and the upper part of this frame may be provided with an internal (guaged) conduit which is evacuable. The lower part is provided with bores, so that the supporting plate P, or even directly a plate-shaped specimen O, can be made to adhere to sample holder S. Specimens 0 having smaller dimensions are placed on supporting plate P and may be covered by a metallic plate R.

For transmission measurements, a waveguide B may be provided above sample holder S, which waveguide again is held in place in a table plane N and is axially displaceable by means of a body L. Upon inserting a specimen O into sample holder S, waveguide B is moved with its open cross-sectional area close toward the surface O. An intermediate plate Z, such as a quartz plate having a thickness of 0.1 to 1 mm, preferably 0.5 mm, may here be inserted instead of cover plate 0'. These plates 0', Z then will occupy the place of the shown sample 0 and cover plate R.

From a radiation source Q, the sharply focused beam of photons or electrons passes through a beam guiding system T to the specimen 0 (see also FIGS. 2,3,4). Sample holder S is connected through a linkage to a displacement mechanism X - Y, so that specimen 0 can be moved to and fro in the zone of the cross-sectional area of waveguide A or B, and irradiated at various locations. Because of the considerably different conditions within the microwave field, it is better to keep the radiation spot on the surface of specimen 0 at a fixed location relative to the field, and, instead, to move the specimen within the cross-sectional area of waveguide A, or B. The beam guiding system T should permit at least a pivotal movement, to be able to adjust the position of the beam. It is also possible, however, to let the beam, or the radiation spot, scan the surface of specimen 0 in such pivotal motion, or even combine the movements of the sample holder and the beam guiding system T.

Figure 6:
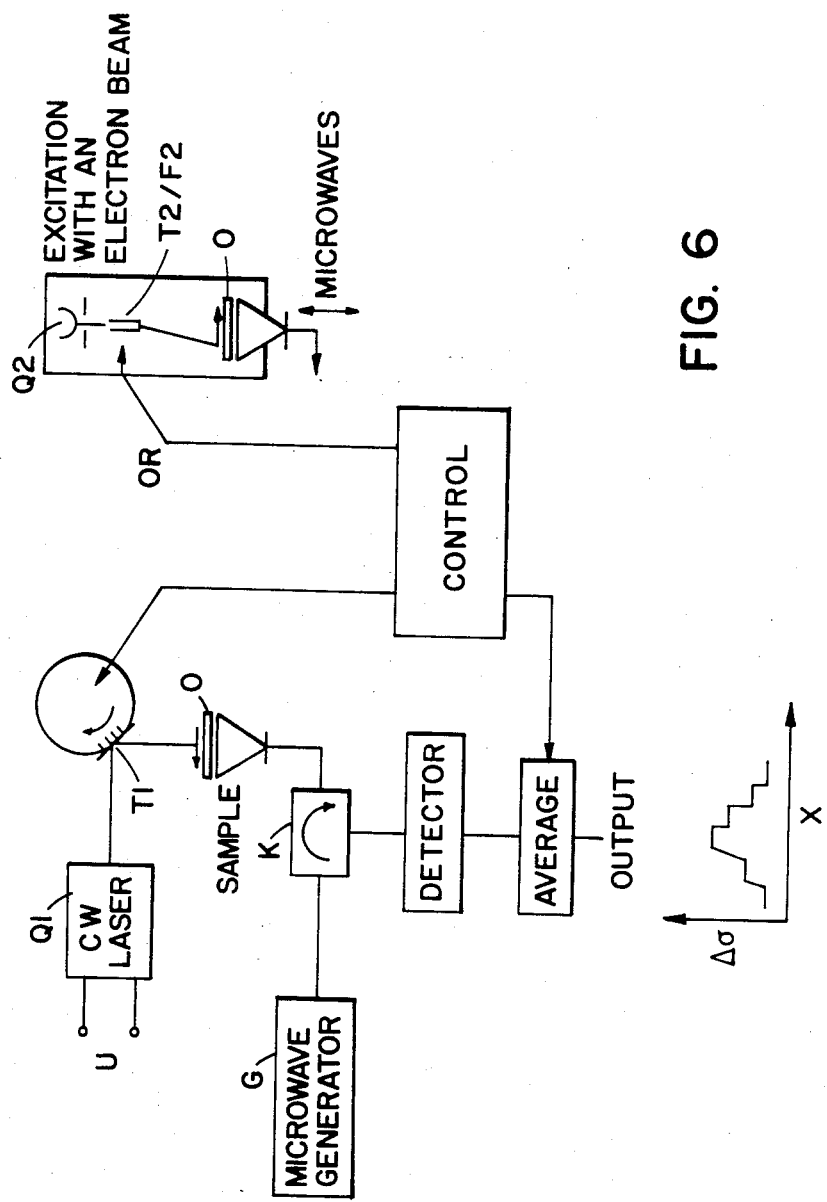
FIG. 6 is a block diagram of a measuring apparatus for determining, in local resolution, the structure and properties of an inhomogeneous semiconductor layer through microwave absorptions.
Figure 7:
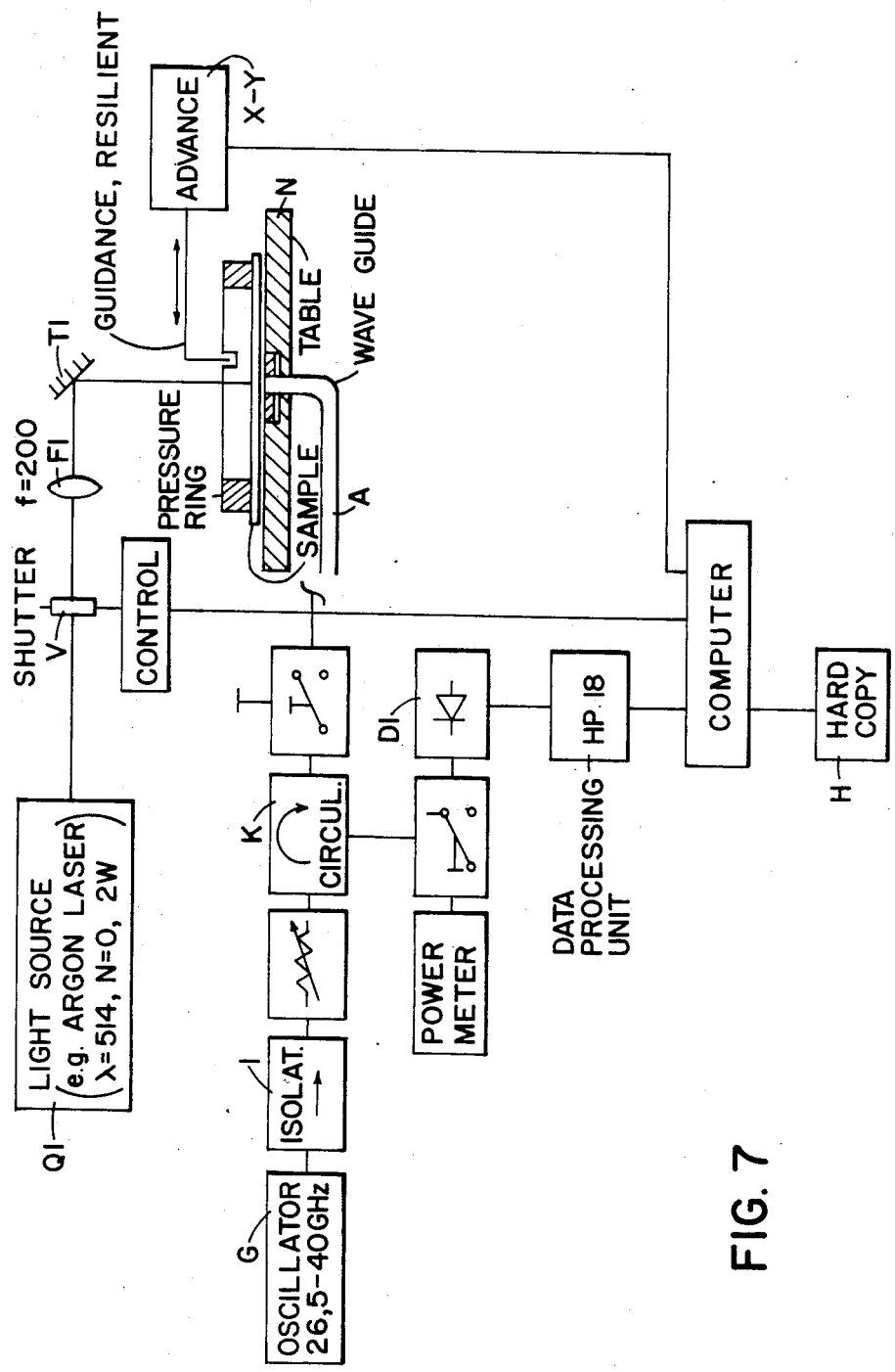
FIG. 7 is a block diagram of another measuring arrangement.

FIGS. 6 and 7 show diagrammatically and in a simplified manner a microwave measuring apparatus and an experimental setup for determining structures, structural defects, in local, or local and time, resolution, of inhomegeneous semiconductor layers. It may be learned from FIG. 6 that both photons, e.g. a CW laser as the source of radiation Q1 and a mechanical-optical beam guiding system T1, and electrons, e.g. an electron beam tube Q2 and an electro-magnetic beam guiding and focusing system T2/F2, may be employed for irradiating a specimen 0. Through a synchronizer and a control, the values measured by detector D1 as reflections of microwaves and exactly associated with the respective irradiated areas of specimens 0, are averaged and, if provided, displayed or delivered as a graphic output. FIG. 7 shows particularly a shutter V in the path of the beam between the photon source Q1 and an optical focusing device F1, permitting measurements in time resolution. Further, for example, between isolator 1 and circulator or directional coupler K, an attenuator of the microwave power is provided, to eliminate overdrives of detector D1 or to adjust the optimum region of unequally sensitive detectors D1.

Figure 8:
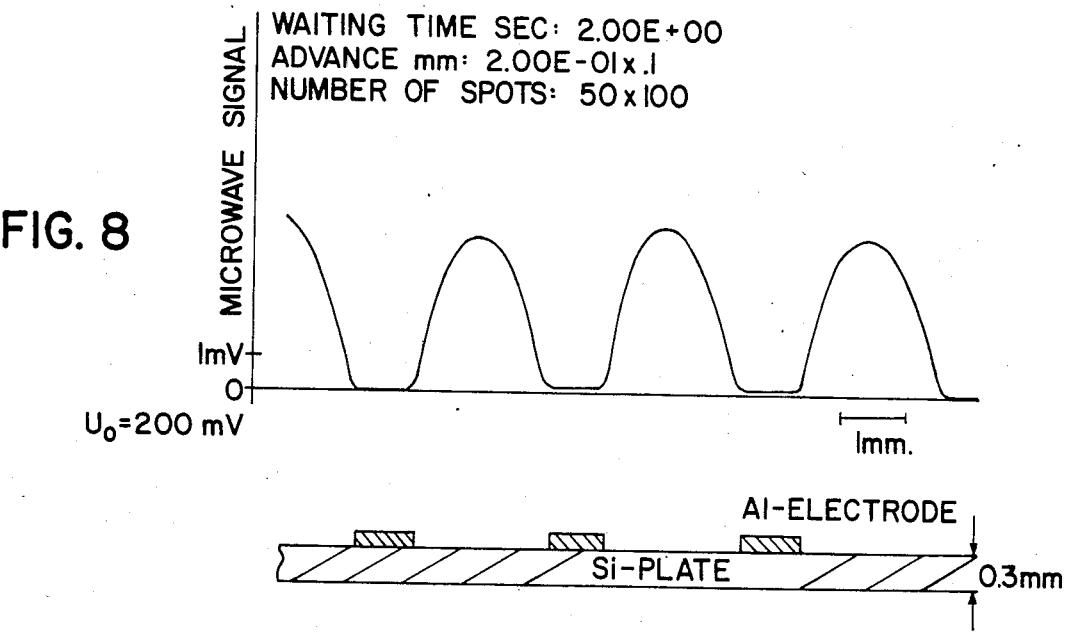
FIG. 8 is a graph generated by the apparatus of FIG. 7, showing a recorded surface profile of an undamaged semiconductor layer.
Figure 9:
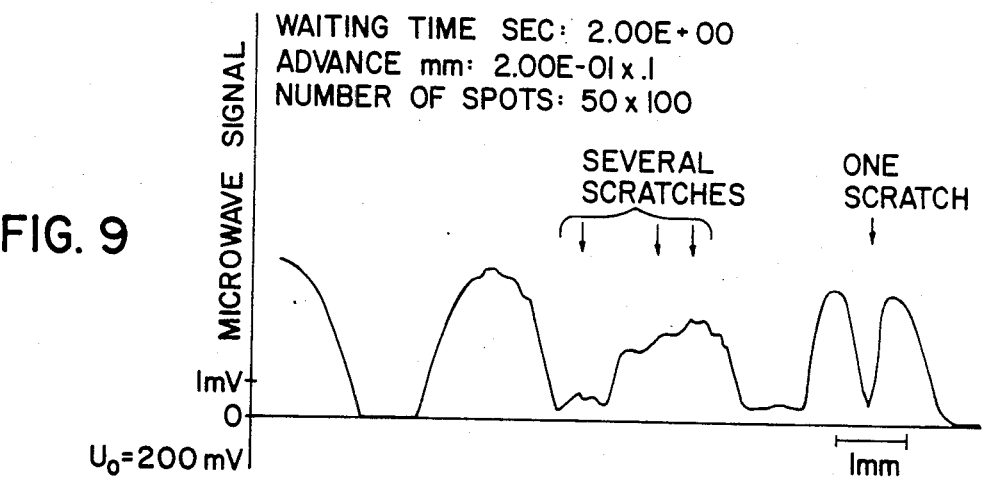
FIG. 9 is a graph corresponding to FIG. 8, showing within the profile also damaged portions of the surface.

The measuring curves of FIGS. 8 and 9 were obtained with Si semiconductor plates having a thickness of 0.3 mm, a diameter of about 50 mm, i.e. a surface of about 2,000 mm$^2$, and being provided with circular Al electrodes having a diameter of 1 mm. The microwave signal shows, in FIG. 8, where the electrodes are provided, and, in FIG. 9, where the surface of the Si or Al, here intentionally, is damaged by scratches.

In these measurements, the radiation spot has been held at a constant location relative to the microwave field, i.e. the specimen has been moved through the cross-sectional area of the waveguide and the beam direction has not been changed. Only relative variations of the microwave reflection or transmission, caused by additionally excited charge carriers in the material of the sample in the zone of the radiation spot (about 0.1 to 10 micrometers in diameter were evaluated). This charge carrier density depends on the structure of the sample, or the surface thereof, so that with x-y displacements, for example, in the micrometer region, a satisfactory high resolution is obtainable for determining the microstructure and/or defects thereof, etc. A computer may be employed for the measurement and evaluation. The invention may also be integrated in microwave detection systems in commercial electron scan microscopes.

The invention is thus a method for the non-destructive contactless testing of a photosensitive material having a surface, comprising exposing the material to a microwave field, irradiating a selected partial area of the surface with a sharply focused beam of radiation selected from the group consisting of electrons and photons, to produce excess charge carriers in the selected partial area which cause variations in the microwave field, measuring the variations in the microwave field which is a measurement of at least one parameter of the material at the selected partial area, and changing the position of the selected partial area over the surface for taking a measurement of the at least one parameter of the material at other location on the surface.

The invention is also an apparatus for the non-destructive contactless testing of photosensitive material which includes a microwave generator for establishing a microwave field, a sample holder for holding a sample of photosensitive semiconductor material to be tested in the microwave field, means for generating radiation selected from the group consisting of electron and photon radiation, means for focusing the radiation into a sharply focused beam which is directed onto a selected portion of a surface of the photsensitive material, a detector for detecting variations in the microwave field due to irradiation of the selected partial area of the material, and means for moving the beam with respect to the material surface so that other selected partial areas are irradiated.

While specific embodiments of the invention have been shown and described in detail to illustrate the application of the principles of the invention, it will be understood that the invention may be embodied otherwise without departing from such principles.

What is claimed is:

1. A method for the non-destructive contactless testing of a photosensitive material having a surface, comprising exposing the material to a microwave field, irradiating a selected partial area of the surface with a sharply focused spot of radiation having a diameter between about 0.1 and about 10.0 micrometers, to produce excess charge carriers at the selected partial area which cause variations in the microwave field, measuring the variations in the microwave field which is a measurement of at least one characteristic of the material at the selected partial area, and changing the position of the selected partial area over the surface for taking a measurement of the at least one characteristic at other locations on the surface, the position being changed by establishing a relative stepwise movement between the spot and the photosensitive material surface while the material remains in the microwave field for changing the position of the selected partial area in stepwise fashion.

2. A method according to claim 1 including moving the spot across the surface of the material for changing the position of the selected partial area, while the material is maintained in the microwave field.

3. A method according to claim 1, including moving the surface of the photosensitive material with respect to the spot while the material remains in the microwave field for changing the position of the selected partial area of the surface.

4. A method according to claim 1, wherein the position of the selected partial area is changed in steps of from 0.1 to 10.0 micrometers.

5. A method according to claim 1, including irradiating the selected partial area using a sharply focused beam of electrons.

6. A method according to claim 1, including irradiating the selected partial area using a beam of photons.

7. A method according to claim 6, including using a CW laser to generate the beam of photons and pulsing the laser to produce a stepwise irradiation of the selected partial area as its position is changed in stepwise fashion.

8. A method according to claim 1, including using a shutter to periodically block a sharply focused beam of irradiation that forms the spot as the position of selected partial area is changed in stepwise fashion.

9. An apparatus for the non-destructive contactless testing of a specimen of photosensitive material having a surface, comprising a sample holder for holding the speciment with its surface lying in a selected plane, a microwave generator for generating microwaves, a waveguide for directing the microwaves to the specimen surface at a selected angle with respect to the selected plane, a microwave detector for detecting microwaves which have interacted with the specimen, the detected microwaves varying due to the creation of a charge carrier excess in the specimen, a radiation generator for generating radiation, beam focusing means associated with the radiation generator for focusing the radiation to a sharply focused beam of radiation having a diameter of about 0.1 to 10.0 micrometers, beam directing means for directing the sharply focused beam against a selected partial area of the specimen surface for creating a charge carrier excess at the partial area which produces microwave variation that are measured by the microwave detector, and displacement means associated with at least one of the beam directing means and the sample holder for establishing a relative stepwise movement between the sharply focused beam and the sample holder to change the location of the partial area on which the beam strikes.

10. An apparatus according to claim 9, wherein the waveguide for microwaves extends substantially to the surface at the partial area to be exposed to the sharply focused beam.

11. An apparatus according to claim 10, wherein the waveguide has a cross-sectional area overlying the partial area to be exposed to the sharply focused beam.

12. An apparatus according to claim 11 wherein the selected angle is 90° so that the waveguide directs microwaves in a direction of propagation which is perpendicular to the selected plane of the specimen surface.

13. An apparatus according to claim 12, wherein the displacement means comprise means for moving the sharply focused beam for changing location of the partial area.

14. An apparatus according to claim 1, including a shutter associated with the beam focusing means and the beam directing means for periodically interrupting the sharply focused beam so that, as the location of the partial area changes, the partial area is irradiated by the beam in stepwise fashion.

15. An apparatus according to claim 1, wherein the radiation generator generates bursts of radiation which are spaced in time.

16. An apparatus according to claim 15, wherein the radiation generator comprises a CW laser which is pulsed to produce stepwise bursts of photon radiation.

17. An apparatus according to claim 1, wherein the waveguide is in the form of an elbow which has an end which extends to the sample holder for supporting the specimen at its surface.

18. An apparatus according to claim 17, wherein the elbow has an aperture therethrough for admitting sharply focused beam.

19. An apparatus according to claim 1, wherein the displacement means comprise a displacement element connected to the specimen holder for moving the specimen holder in the selected plane of the specimen surface.

20. An apparatus according to claim 1, including a computer connected to the displacement means, the radiation generator and the beam directing means for changing the location of the partial area.

21. An apparatus according to claim 9 wherein said radiation generator for generating radiation generates a beam of electrons.

* * * * *

UNITED STATES PATENT AND TRADEMARK OFFICE
CERTIFICATE OF CORRECTION

PATENT NO. : 4,704,576

DATED : November 3, 1987

INVENTOR(S) : Tributsch et al

It is certified that error appears in the above-identified patent and that said Letters Patent is hereby corrected as shown below:

On the title page assignee should read

--(73) Assignee: Hahn-Meitner-Institut Berlin GmbH --.

Signed and Sealed this

Twenty-sixth Day of April, 1988

Attest:

DONALD J. QUIGG

Attesting Officer     Commissioner of Patents and Trademarks